United States Patent [19]

Strebelle

[11] Patent Number: 5,068,474
[45] Date of Patent: Nov. 26, 1991

[54] PROCESS FOR THE PURIFICATION OF VINYL CHLORIDE

[75] Inventor: Michel Strebelle, Brussels, Belgium

[73] Assignee: Solvay & Cie, Brussels, Belgium

[21] Appl. No.: 531,458

[22] Filed: May 31, 1990

[30] Foreign Application Priority Data

Jun. 2, 1989 [FR] France ................. 89 07503

[51] Int. Cl.$^5$ ............................................ C07L 17/38
[52] U.S. Cl. .................................................. 570/238
[58] Field of Search ......................................... 570/238

[56] References Cited

U.S. PATENT DOCUMENTS 2,816,148 12/1957 Anderson et al. ................. 590/238

Primary Examiner—Howard T. Mars
Attorney, Agent, or Firm—Spencer & Frank

[57] ABSTRACT

Process for the removal from vinyl chloride of compounds of ester type by an operation of treatment comprising an alkaline washing and a treatment with a hydride.

5 Claims, 1 Drawing Sheet

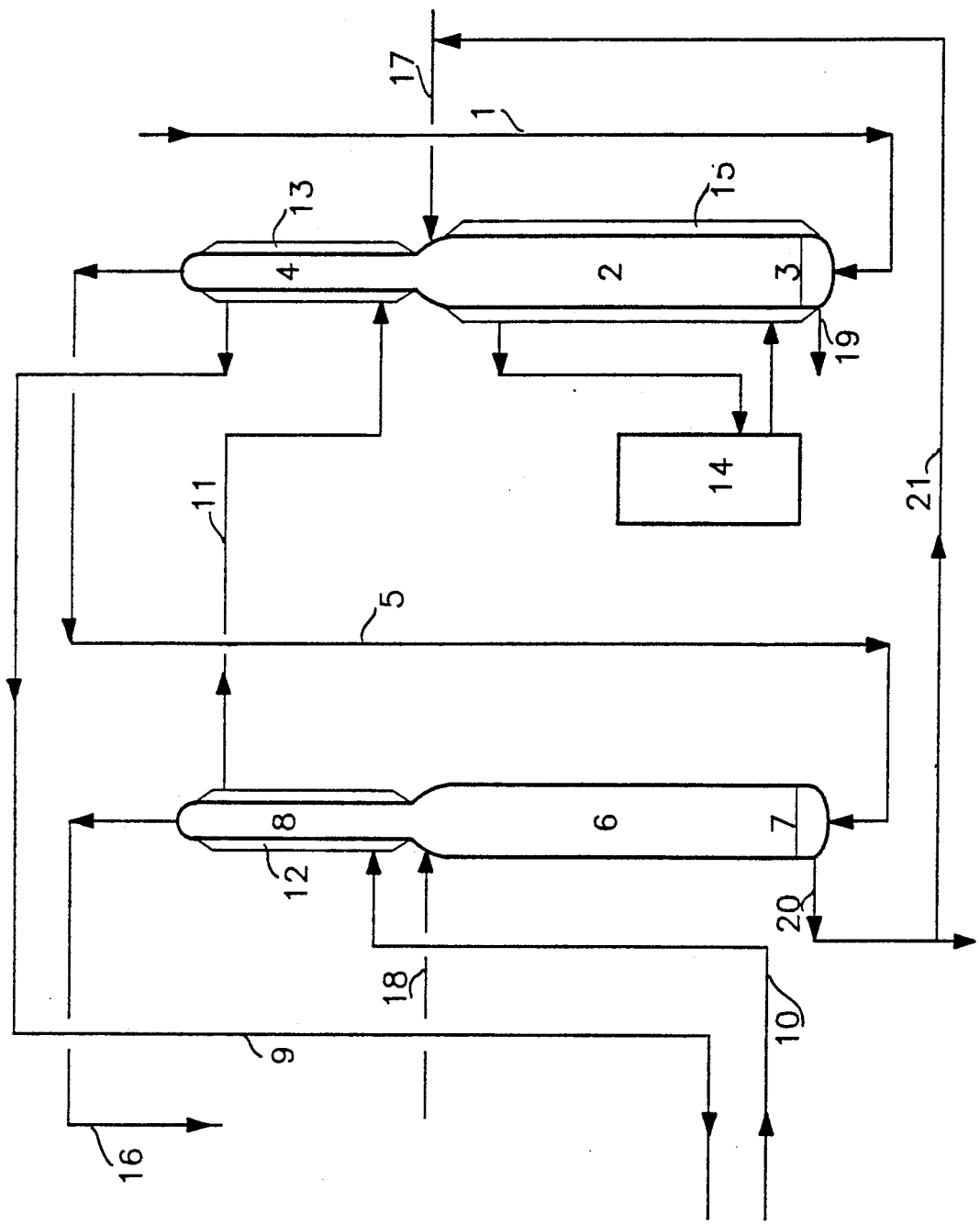

PROCESS FOR THE PURIFICATION OF VINYL CHLORIDE

FIELD OF THE INVENTION

The present invention relates to a process for the removal from vinyl chloride of compounds of the ester type and more particularly from ester compounds containing an unsaturation in the molecule, such as vinyl acetate.

TECHNOLOGY REVIEW

It is known that the vinyl chloride employed in industry is a compound which can be obtained according to various methods of manufacture which have been optimized so as to produce a compound whose purity is high and, in all cases, sufficient for the uses to which this compound is usually intended and most particularly for its homopolymerization.

A completely different problem which has recently arisen in industry, for economic and environmental reasons, is the problem presented by the purification of residual vinyl chloride, unconverted or originating from industrial processes in which it has been used. In this context the problem presented by the separation of vinyl chloride from esters such as vinyl acetate occupies a special place, since it relates to the separation of two comonomers resulting from a copolymerization operation in which, for lack of a satisfactory solution in respect of the recycling of the two comonomers, it was accepted to lose all or some of the two monomers using nonselective destructive operations such as burning.

SUMMARY OF THE INVENTION

A new process has now been found which does not have the abovementioned disadvantages and which, by destroying solely the ester compound, enables very pure vinyl chloride to be recovered, and this makes it possible to employ it for an application identical with that of a vinyl chloride originating directly from a production unit.

To this end, the present invention relates to a process for the removal from vinyl chloride of compounds of ester type exhibiting a structure of enol esters, characterized in that the vinyl chloride undergoes a treatment comprising an alkaline washing stage followed or accompanied by a stage of treatment with a hydride and preferably with a borohydride.

BRIEF DESCRIPTION OF THE DRAWING

The Figure is a diagram of a plant in which the process of the present invention can be carried out, either batched or continuously.

DETAILED DESCRIPTION OF THE INVENTION

The ester-type compounds which are generally present in vinyl chloride are ester compounds which have an unsaturation in their molecule, which makes them capable of copolymerizing with vinyl chloride by a radical route. A compound of this kind which has produced good results is vinyl acetate. It is obvious, however, that the process of the invention is readily applied to any type of unsaturated ester exhibiting an enol ester structure which may be found in vinyl chloride for any reasons whatever.

The stage of alkaline washing of the impure vinyl chloride can in principle be carried out with any known basic agent, but is usually carried out with an aqueous solution of a base derived from alkali or alkaline-earth metals. This treatment is preferably carried out with a hydroxide of these metals. Finally, good results have been obtained with sodium hydroxide. Although the present invention is not intended to be limited in any way or to be subject to any scientific explanation or theory, it is highly probable that the alkaline treatment converts all the ester compound to a salt and an aldehyde. Thus, more particularly in the case of vinyl acetate, sodium acetate and acetaldehyde would appear to be formed at this stage when the process is performed using sodium hydroxide.

When the alkaline washing stage is carried out with an aqueous solution of sodium hydroxide, the NaOH concentration is generally between 0.01 M/l and 10 M/l and preferably between 0.1 M/l and 2 M/l.

The alkaline washing stage is followed by a stage of treatment of the vinyl chloride with a hydride and more particularly a borohydride such as sodium borohydride, and this has the result of purifying the vinyl chloride probably by removing aldehydes such as the residual acetaldehyde present in the mixture.

The sodium borohydride treatment has the additional advantage of converting aldehydes such as acetaldehyde into alcohols by a reduction reaction which can be carried out in an alkaline medium. Consequently, it becomes technically possible to condense the alkaline washing of the first stage and the borohydride treatment into a single operation. At the present time, however, such an operation does not constitute the industrially preferred solution, but this is solely due to the high price of borohydrides. Meanwhile, a solution which has given good results consists in operating in two distinct stages, while returning a part or all of the aqueous effluent from the second stage, which inescapably contains a part of borohydride, to the reactor of the first stage, in which the alkaline washing takes place. This solution, for its part, would appear to offer the advantage of a reduction of the carbonyl functional groups of the heavy products originating from a possible aldolization of the aldehydes formed during the alkaline washing of the first stage, and of reducing the fouling which is necessarily linked with the presence of such heavy products.

When the process of the invention involves sodium borohydride, the latter is generally used in basic aqueous solution such as a sodium hydroxide solution whose concentration may vary between 0.1 M/l and 10 M/l and preferably between 1 and 5 M/l. The concentration of NaBH$_4$ in this alkaline solution is generally between 0.01 M/l and the solubility limit of NaBH$_4$ in this alkaline solution; however, the concentration of NaBH$_4$ is preferably between 0.1 and 1 M/l.

Apart from the abovementioned stages, whose operational sequence is essential for obtaining esterfree vinyl chloride, the process of the invention may provide other stages according to the particular conditions which have led to such a vinyl chloride.

When carried out using sodium borohydride on vinyl chloride originating from a manufacture of copolymerization of vinyl chloride and vinyl acetate, the process of the invention can be carried out in temperature conditions of between 0° and 70° C. and preferably between 0° and 10° C. insofar as the alkaline washing stage is concerned and between 10° and 70° C. and preferably between 15 and 35° C. insofar as the reduction stage is concerned.

With regard to the pressure conditions, these are not critical and are usually between 1 and 10 bars in the case of both stages. The two stages are usually performed at atmospheric pressure.

The process of the invention can be carried out in any plant allowing the stages described above to be performed and comprising immersed, sprayed columns optionally equipped with a packing and capable of operating either batchwise or continuously. A diagram of a plant which has given good results is reproduced in FIG. 1 and comprises:

- a conduit 1 by which gaseous vinyl chloride containing the ester to be removed is introduced into the system,
- a first reactor 2, equipped with a jacket 15, into which the impure vinyl chloride is introduced via the conduit 1. This reactor 2 is advantageously equipped with a device for distributing gases into the liquid 3 and with a condenser 4 permitting good bubbling of the gases to be carried out and the liquid products to be retained at the alkaline washing temperature respectively,
- a conduit 5 connecting the condenser 4 of the reactor 2 to a second reactor 6 intended for carrying out the borohydride treatment,
- this reactor 6 is again advantageously equipped with a device for distributing gases into the liquid 7 and with a condenser 8 whose functions are identical with those of the device 3 and of the condenser 4,
- the pure vinyl chloride is then conveyed by the conduit 16 to the drying followed by a recompression and a liquefaction in order to permit the storage of pure vinyl chloride,
- finally, the plant is completed by a refrigeration circuit enabling, via the conduits 10 and 11, the condensers 4 and 8 to be cooled using the jackets 12 and 13 and, using an independent refrigeration circuit 14, the cooling of the jacket 15 of the alkaline washing reactor 2 to be ensured respectively.

In addition, the reactors 2 and 6 may be equipped for functioning continuously or noncontinuously. To this end, conduits 17 and 18 are provided in order to feed them with aqueous solutions of NaOH and of NaOH and borohydride respectively. Furthermore, in order to keep the level constant in the reactors 2 and 6, the latter also comprise "purge" conduits 19 and 20, which enable the partially exhausted aqueous solutions to be removed. Finally, the plant comprises a conduit 21 which allows the conduits 17 and 20 to be connected so as to make it possible to return all or part of the aqueous effluent from the reactor 6 continuously or noncontinuously into the reactor 2.

The plant may be made wholly or partially of any suitable material, coated or otherwise with polymeric compounds which make it possible to improve the resistance of the materials to some of the reactants used. The whole plant is usually made of stainless steel.

The vinyl chloride recovered at the outlet of the second reactor can be employed in any manufacture and more particularly for the manufacture of high-purity homopolymers.

Lastly, although the invention relates to the removal from vinyl chloride of compounds of unsaturated ester type exhibiting an enol ester structure, it is obvious that it can also result, without other fundamental modification, in the purification of other alkyl halides of the same type, such as vinylidene chloride, vinyl fluoride and vinylidene fluoride, as well as the removal from these compounds of ketonic or aldehyde impurities of an origin other than the enol ester.

The invention is illustrated by the following examples.

EXAMPLES 1

The operation is carried out in a plant such as illustrated in FIG. 1, in which the column 2 and the column 6 have a diameter of 65 mm, a height of 550 mm and a liquid capacity of 400 cm$^3$.

Column 2, kept at a temperature of 6° C. by cooling, contains a 1-molar solution of NaOH and the composition at the bottom of column 6, kept at 25° C., consists of a 1-molar solution of NaBH$_4$ in a 2.5-molar aqueous solution of NaOH.

Vinyl chloride recovered from a plant for copolymerization with vinyl acetate is introduced into this plant via the conduit 1 at a gas flow rate of approximately 145 Nl/h (i.e. normal litres measured at 0° C. and at atmospheric pressure/hour).

Five tests carried out with vinyl acetate contents of between 360 (test 3) and 47,000 ppm vol. (test 5) have led to the results and observations summarized in Table 1.

TABLE 1

|  | TEST NUMBER | | | | |
|---|---|---|---|---|---|
|  | 1 | 2 | 3 | 4 | 5 |
| Test conditions | | | | | |
| Alkali reactor: | | | | | |
| NaOH in mol/l | 1 | 1 | 1 | 1 | 1 |
| Volume in cm$^3$ | 400 | 400 | 400 | 400 | 400 |
| Temperature in °C. | 6 | 6 | 6 | 6 | 6 |
| Reactor with: | | | | | |
| NaBH$_4$ in mol/l | 1 | 1 | 1 | 1 | 1 |
| NaOH in mol/l | 2.5 | 2.5 | 2.5 | 2.5 | 2.5 |
| Volume in cm$^3$ | 400 | 400 | 400 | 400 | 400 |
| Temperature in °C. | 25 | 25 | 25 | 25 | 25 |
| Treated gas flow rate: in Nl/h | 146.1 | 145.6 | 145.3 | 146.3 | 142.2 |
| Test duration: | 1.5 | 1.75 | 2.3 | 1.3 | 0.83 |
| VPC* analyses | | | | | |
| Alkali reactor entry (column 2): Vinyl acetate in ppm by vol. | 1,900 | 650 | 360 | 8,400 | 47,000 |
| NaBH$_4$ reactor entry (column 6): | | | | | |

TABLE 1-continued

| | TEST NUMBER | | | | |
|---|---|---|---|---|---|
| | 1 | 2 | 3 | 4 | 5 |
| Vinyl acetate in ppm by vol. | <1 | 3,1 | <1 | <1 | 10 |
| Acetaldehyde in ppm by vol. | 220 | 140 | 46 | 231 | 1,700 |
| NaBH$_4$ reactor exit (column 6): | | | | | |
| Vinyl acetate in ppm by vol. | <1 | <1 | <1 | <1 | <1 |
| Acetaldehyde in ppm by vol. | <1 | <1 | <1 | <1 | <1 |
| Ethanol in ppm by vol. | 37 | 36 | 53 | 22 | 229 |
| Results | | | | | |
| Conversion of vinyl acetate in the alkali reactor in % | 100 | 99.5 | 100 | 100 | 99.98 |
| Conversion of vinyl acetate in the NaBH$_4$ reactor in % | — | 100 | — | — | 100 |
| Acetaldehyde at exit of alkali reactor relative to the vinyl acetate used, in mol % | 11.6 | 21.5 | 12.8 | 2.75 | 3.6 |
| Conversion of acetaldehyde at NaBH$_4$ reactor exit in mol % | 100 | 100 | 100 | 100 | 100 |

*Vapour phase chromatography

In the light of the above results it may be concluded that the process of the invention makes it possible to remove quantitatively the vinyl acetate present in vinyl chloride and that the latter consequently has a purity enabling it to be recycled to any process, including homopolymerization.

EXAMPLE 2

The operation is carried out in a plant and in temperature conditions identical with those of Example 1 but with a 0.5 M alkaline solution of NaOH in column 2 and a 0.1 M solution of NaBH in a 2.5 M aqueous solution of NaOH in column 6.

The test is carried out with vinyl acetate contents of 23,000 ppm by volume in the gaseous vinyl chloride conveyed at a gas flow rate of approximately 60 Nl/h in the case of 400 cm$^3$ of liquid heel.

At the entry of the NaBH$_4$ reactor the vinyl chloride contains 2,318 ppm of acetaldehyde in the case of 18 ppm of vinyl acetate and, at the outlet of this reactor, contents of less than 1 ppm by volume of these two impurities are observed with an appearance of only 39 ppm of ethanol.

EXAMPLE 3

The operation is carried out in conditions identical with those of Example 2 but with a 0.5 M alkaline solution of NaOH in column 2.

The plant employed is, for its part, that of Examples 1 and 2, modified so as to permit the recycling of a part of the liquid from column 6 towards column 2.

The test is carried out with a recycle flow rate of a part of the partially purified liquid from column 6 towards column 2 of 4 cm$^3$/hour for 1 week via the conduits 20, 21 and 17 and the levels are kept constant in the reactors 2 and 6 by adjusting the feed rates of fresh solutions.

Apart from the results already discussed in Example 2, during this test it is observed that the hydride recycled to column 2 has apparently completely disappeared 5 minutes after the beginning of the experiment and that, throughout the experiment, the liquid medium in column 2 remains clear and perfectly liquid and that there is no formation of precipitates in this column, which is not the case in the experiments of Examples 1 and 2, in which the formation of solid products is observed, colouring the reaction mixture and forming precipitates.

What is claimed is:

1. A process for the removal of an unsaturated ester compound exhibiting an enol ester structure from vinyl chloride comprising treating impure vinyl chloride with an alkaline wash followed or accompanied by an aqueous treatment with sodium borohydride.

2. The process according to claim 1, wherein the alkaline wash is carried out with an aqueous solution of a base derived from alkali or alkaline-earth metals.

3. Process according to claim 1, wherein the alkaline wash is followed by treatment with sodium borohydride.

4. The process according to claim 2, wherein a part or all of the aqueous effluent from the sodium borohydride treatment is recycled to the alkaline wash.

5. The process according to claim 1, wherein the unsaturated ester compound present in the impure vinyl chloride is vinyl acetate.

* * * * *